United States Patent
Kim (10) Patent No.: US 7,292,716 B2
(45) Date of Patent: Nov. 6, 2007

(54) MEDICAL SIMULATION APPARATUS AND METHOD FOR CONTROLLING 3-DIMENSIONAL IMAGE DISPLAY IN THE MEDICAL SIMULATION APPARATUS

(75) Inventor: Han-Joon Kim, Kobe (JP)

(73) Assignee: Imagnosis Inc., Hyogo (JP)

( * ) Notice: Subject to any disclaimer, the term of this patent is extended or adjusted under 35 U.S.C. 154(b) by 657 days.

(21) Appl. No.: 10/493,968

(22) PCT Filed: Oct. 31, 2002

(86) PCT No.: PCT/JP02/11337

§ 371 (c)(1),
(2), (4) Date: Apr. 29, 2004

(87) PCT Pub. No.: WO03/037204

PCT Pub. Date: May 8, 2003

(65) Prior Publication Data

US 2004/0259057 A1 Dec. 23, 2004

(30) Foreign Application Priority Data

Oct. 31, 2001 (JP) .............................. 2001-335081

(51) Int. Cl.
*G06K 9/00* (2006.01)
*G06T 15/00* (2006.01)
*A61C 11/00* (2006.01)
*A61C 19/04* (2006.01)

(52) U.S. Cl. ..................... 382/128; 382/103; 382/154; 345/419; 433/54; 433/68

(58) Field of Classification Search ................ 382/103, 382/106, 107, 128, 131, 154; 348/77; 345/419; 433/68, 69, 54, 55, 56, 57
See application file for complete search history.

(56) References Cited

U.S. PATENT DOCUMENTS

| 5,278,756 A | * | 1/1994 | Lemchen et al. ............ 600/587 |
| 5,338,198 A | * | 8/1994 | Wu et al. .................... 433/213 |
| 5,340,309 A | * | 8/1994 | Robertson ..................... 433/69 |
| 5,454,717 A | * | 10/1995 | Andreiko et al. ............. 433/24 |

(Continued)

FOREIGN PATENT DOCUMENTS

JP        10-66706        3/1998

(Continued)

*Primary Examiner*—Andrew W. Johns
*Assistant Examiner*—Anthony Mackowey
(74) *Attorney, Agent, or Firm*—Rabin & Berdo, P.C.

(57) ABSTRACT

A medical simulation apparatus is provided, which is capable of performing a simulation by correlating a three-dimensional image with an entity model.

Coordinates of measurement marks MP1, MP2, MP3 on a surface of a lower dental arch model 62 in a coordinate system defined by three reference marks MK1, MK2, MK3 are acquired before and after displacement of the lower dental arch model 62. The coordinates thus acquired are converted into coordinates in a coordinate system defined by reference marks PK1, PK2, PK3 on the basis of a relationship between the reference marks MK1, MK2, MK3 and the reference marks PK1, PK2, PK3. Then, changes in the coordinates after displacement of the lower dental arch model 62 are determined, and a region preliminarily specified in a three-dimensional image displayed on a display 5 is displaced on the basis of the coordinate changes thus determined.

4 Claims, 7 Drawing Sheets

U.S. PATENT DOCUMENTS

| | | | | |
|---|---|---|---|---|
| 5,605,459 | A | * | 2/1997 | Kuroda et al. ............... 433/214 |
| 5,842,858 | A | * | 12/1998 | Truppe ........................ 433/69 |
| 5,879,158 | A | * | 3/1999 | Doyle et al. .................. 433/24 |
| 6,152,731 | A | * | 11/2000 | Jordan et al. .................. 433/69 |
| 6,947,038 | B1 | * | 9/2005 | Anh et al. .................. 345/419 |
| 7,110,594 | B2 | * | 9/2006 | Jones et al. .................. 382/154 |
| 7,123,767 | B2 | * | 10/2006 | Jones et al. .................. 382/154 |
| 7,234,937 | B2 | * | 6/2007 | Sachdeva et al. ............. 433/24 |
| 2004/0166469 | A1 | * | 8/2004 | Tremont ........................ 433/68 |
| 2005/0251281 | A1 | * | 11/2005 | O'Brien et al. ............. 700/119 |

FOREIGN PATENT DOCUMENTS

| JP | 2001-112743 | | 4/2001 |
|---|---|---|---|
| JP | 2002015338 | A * | 1/2002 |

* cited by examiner

MEDICAL SIMULATION APPARATUS AND METHOD FOR CONTROLLING 3-DIMENSIONAL IMAGE DISPLAY IN THE MEDICAL SIMULATION APPARATUS

TECHNICAL FIELD

The present invention relates to a medical simulation apparatus for performing a simulation of a surgical operation, for example, for confirmation of a surgical technique and prediction of a postoperative state, and to a three-dimensional image display controlling method for the medical simulation apparatus.

PRIOR ART

In the medical field, a simulation is often performed with the use of a trace of a radiograph or an entity model (formed of gypsum plaster, a resin or the like). On the basis of the results of the simulation, a surgical technique is confirmed and a postoperative state is predicted. Where a surgical orthodontic operation is performed for treatment of protrusion of an upper jawbone or a lower jawbone (so-called buck teeth or protruding lower lip) or jaw deformity in dental surgery or plastic surgery, for example, a simulation is performed for confirmation of a surgical technique and prediction of a postoperative state.

Figure 7:
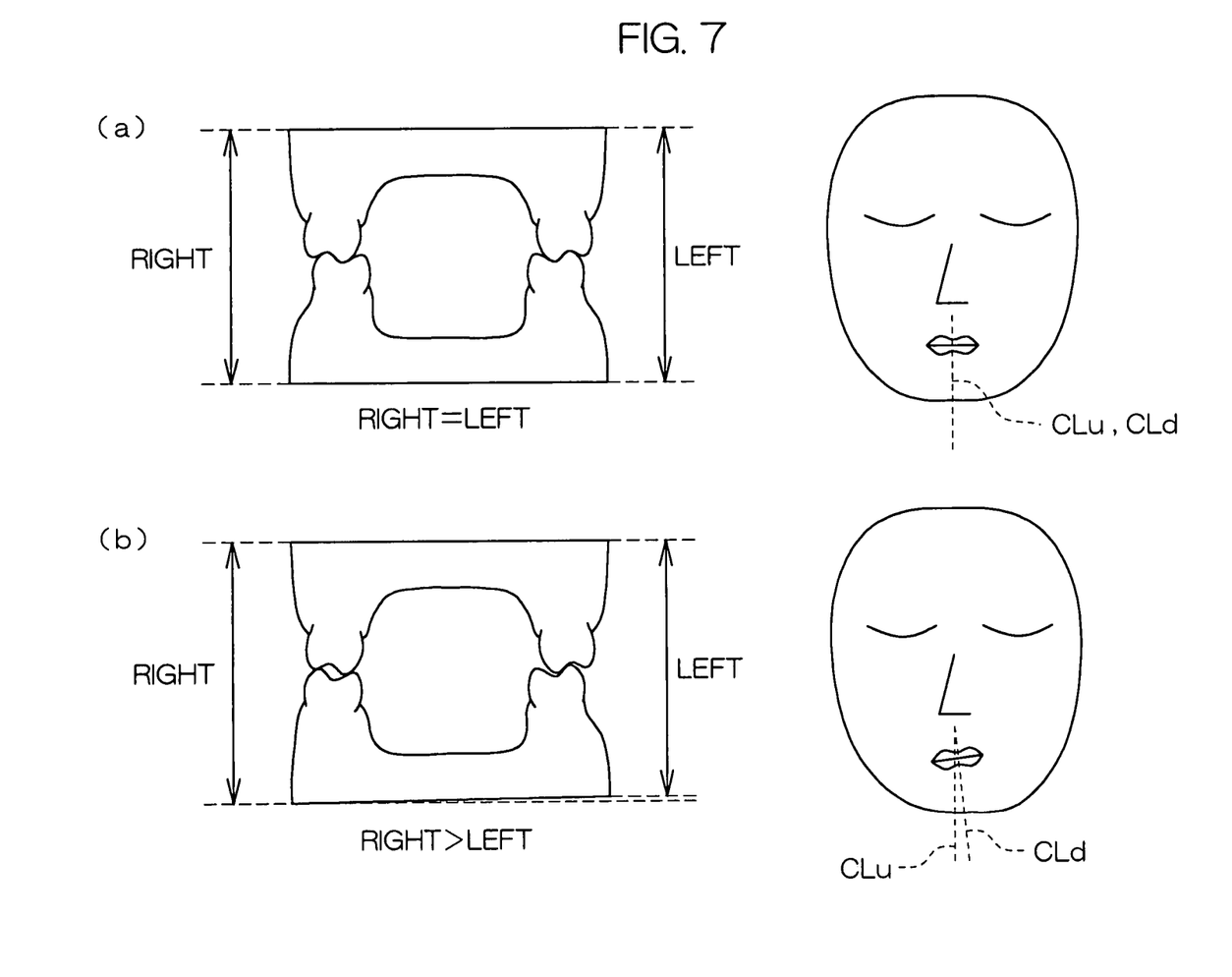
FIG. 7 are diagrams for explaining why a simulation is required for a surgical orthodontic operation.

In the surgical orthodontic operation, occlusion of upper and lower dental arches cannot be ignored for positioning of the upper and lower jawbones. Occlusal surfaces of teeth (molars) have raised cusps and fissures recessed between the cusps. Therefore, an occlusal height (a distance between the upper and lower jawbones) differs between a case where cusps of upper teeth are in contact with cusps of lower teeth and a case where cusps of the upper or lower teeth are in contact with fissures of the lower or upper teeth. Where the occlusion is such that the cusps of the upper or lower teeth are in contact with the fissures of the opposed lower or upper teeth on right and left sides as shown in FIG. 7(*a*), for example, a median line CLu of the upper dental arch is aligned with a median line CLd of the lower dental arch. However, where the cusps of the upper teeth are in contact with the cusps of the lower teeth on the right side and the cusps of the upper or lower teeth are in contact with the fissures of the opposed lower or upper teeth on the left side as shown in FIG. 7(*b*), the occlusal height on the right side is greater than the occlusal height on the left side, so that the median line CLd of the lower dental arch is inclined. In this case, it is clinically necessary to displace or grind teeth for improvement of a teeth contact state. In order to confirm postoperative problems and solutions to the problems, various simulations are conventionally performed for a surgical orthodontic operation for displacing a jawbone (particularly, the lower jawbone).

For example, a simulation (paper surgery) is performed with the use of a standard radiograph of a head or a photograph of a face. In the paper surgery which is a simulation for predictive diagnosis on skeletal balance, a change in skeletal morphology after the surgical orthodontic operation can be checked. However, it is impossible to check a teeth contact state, because the paper surgery provides only two-dimensional information. Therefore, a simulation (model surgery) is also performed with the use of a dental arch model. The predictive diagnosis on the occlusal state is carried out on the basis of the model surgery.

However, it is difficult to reflect and correlate the two-dimensional image information obtained through the paper surgery and the three-dimensional image information obtained through the model surgery with respect to each other. Therefore, a facial appearance change attributable to the teeth contact state cannot be predicted by the combination of the paper surgery and the model surgery.

In recent years, an apparatus has been developed, which is capable of stereographically reconstructing multiple tomographic data obtained by a tomographic apparatus such as a CT apparatus or an MRI apparatus on a computer, displaying the resulting three-dimensional image (stereographic image) on a display, and performing a simulation with the use of the three-dimensional image on the display. The existing apparatus is capable of cutting away a desired portion of the three-dimensional image and three-dimensionally displacing the cut-away portion on the display. However, it is difficult to cut away an image portion of the lower jawbone and displace the cut-away image portion to ensure proper contact between the upper and lower dental arches without any overlap. This makes it impossible to check the teeth contact state on the display, and to check the facial appearance change attributable to the teeth contact state.

DISCLOSURE OF THE INVENTION

In view of the foregoing, it is an object of the present invention to provide a medical simulation apparatus which is capable of performing a simulation by correlating a three-dimensional image with an entity model.

It is another object of the present invention to provide a three-dimensional image display controlling method for a medical simulation apparatus which is capable of performing a simulation by correlating a three-dimensional image with an entity model.

According to a first inventive aspect of the invention, to achieve the aforesaid objects, there is provided a medical simulation apparatus, which comprises: image display means (5) which displays a three-dimensional image of a patient; and display controlling means which correlates an entity model (6, 8, 9, 10) of the patient with the three-dimensional image by utilizing at least three reference points (MK1, MK2, MK3) on the entity model and at least three reference points (PK1, PK2, PK3) on the three-dimensional image, and changes the three-dimensional image according to a change in the entity model.

According to a second inventive aspect of the invention, the above-described medical simulation apparatus is characterized in that: the change in the entity model includes displacing a predetermined portion of the entity model; and the display controlling means determines changes in coordinates of points on the three-dimensional image corresponding to at least three points (MP1, MP2, MP3) on the predetermined portion after the displacement of the predetermined portion on the basis of a relationship between the reference points on the entity model and the reference points on the three-dimensional image, and displaces a region of the three-dimensional image corresponding to the predetermined portion on the basis of the determined coordinate changes.

According to a third inventive aspect of the invention, the medical simulation apparatus is further characterized in that the entity model comprises upper and lower dental arch models, and the predetermined portion is the upper dental arch model or the lower dental arch model.

It is noted that the parenthesized alphanumeric characters denote corresponding components in the following embodiments, and this definition is applicable to the following description.

According to the present invention, the three-dimensional image displayed on the image display means can be changed according to the change in the entity model.

According to the above-described second inventive aspect of the invention, when the predetermined portion of the entity model is displaced, the corresponding region of the three-dimensional image of the patient displayed on the image display means is correspondingly displaced. With the use of the medical simulation apparatus, the upper dental arch model and the lower dental arch model, for example, are produced, and the lower dental arch model is displaced with respect to the upper dental arch model so that the contact state of the upper dental arch and the lower dental arch is optimized. Thus, functional information such as the contact state of the upper dental arch and the lower dental arch can be reflected on the change in the three-dimensional image of the patient. On the basis of the change in the three-dimensional image, a dentist can determine where a lower jawbone to be displaced by a surgical orthodontic operation is to be fixed, which tooth is to be displaced and how the tooth is to be displaced through postoperative orthodontics, in order to achieve an optimum occlusal state and an optimum morphological change of the entire head. In this case, the entity model comprises the upper and lower dental arch models, and the predetermined portion of the entity model corresponds to the lower dental arch model.

The entity model may be a model formed of gypsum plaster or a resin material on the basis of the entity of the patient. In this case, the predetermined portion corresponds to a portion of the entity of the patient to be displaced by the surgical operation.

According to a fourth inventive aspect of the invention, the medical simulation apparatus according to any of the previously described aspects is further characterized in that: the change in the entity model includes providing a dot or a line on the entity model; and the display controlling means determines coordinates of a point or points on the three-dimensional image corresponding to the dot or points on the line provided on the entity model on the basis of the relationship between the reference points on the entity model and the reference points on the three-dimensional image, and displays an image of the dot or the line provided on the entity model in the three-dimensional image on the basis of the determined point coordinates.

According to the present invention, the dot or the line provided on the entity model can be displayed in the three-dimensional image with fidelity.

If addition of a foreign component such as a dental implant to the entity model is regarded as the provision of the line on the entity model, for example, a simulation of the implantation of the dental implant can be performed.

Where a dental implant is to be implanted in a jawbone, it is a conventional practice to perform a simulation (paper surgery) utilizing a standard radiograph of a head or a photograph of a face and a simulation (model surgery) utilizing dental arch models for examination of the implantation direction and depth of the dental implant. However, it is difficult to reflect and correlate two-dimensional image information obtained through the paper surgery and three-dimensional image information obtained through the model surgery with respect to each other. An attempt has recently been made to examine the implantation direction and depth of the dental implant through a simulation utilizing a three-dimensional image based on multiple tomographic data obtained by a tomographic apparatus such as a CT apparatus or an MRI apparatus and through the model surgery. However, even if the simulation of the implantation of the dental implant in the dental arch model is performed on the basis of the implantation direction and depth of the dental implant examined on the three-dimensional image, it is impossible to check if the results of the simulation are consistent with the examination on the three-dimensional image.

According to the present invention, on the contrary, the dentist can check if the implantation direction and depth of the dental implant are appropriate, by implanting the dental implant in the entity model and displaying an image of the implanted dental implant in the three-dimensional image. Thus, the dentist can properly determine the implantation direction and depth of the dental implant.

According to a fifth inventive aspect of the invention, there is provided a three-dimensional image display controlling method for a medical simulation apparatus, the method comprising: displaying a three-dimensional image of a patient on image display means (5); correlating an entity model with the three-dimensional image by utilizing at least three reference points (MK1, MK2, MK3) on the entity model and at least three reference points (PK1, PK2, PK3) on the three-dimensional image; and changing the three-dimensional image displayed on the image display means according to a change in the entity model.

This method provides the same effects as described in relation to the above-described first aspect of the invention.

EMBODIMENTS OF THE INVENTION

Embodiments of the present invention will hereinafter be described in detail with reference to the attached drawings.

Figure 1:
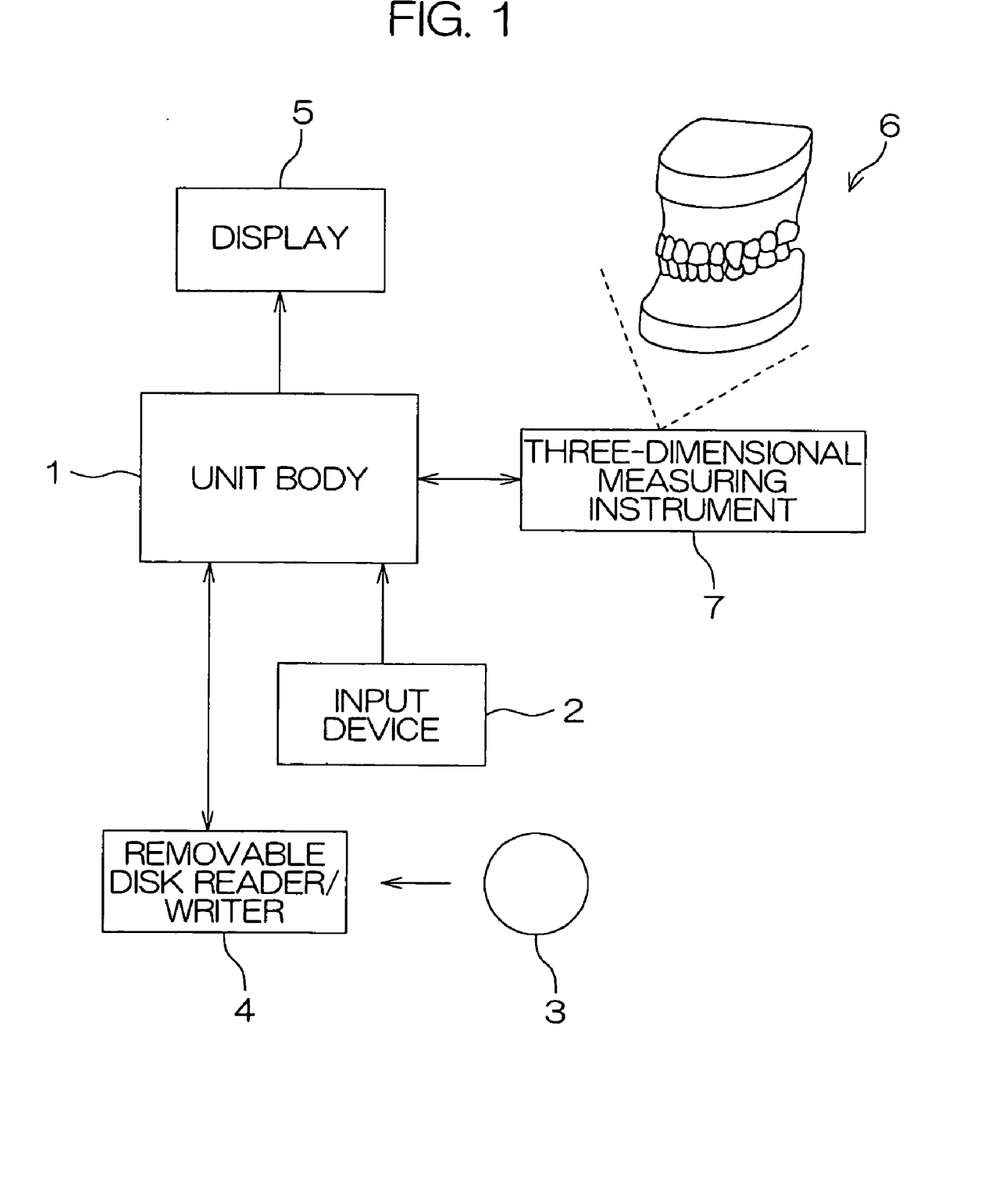
FIG. 1 is a block diagram illustrating the construction of a medical simulation apparatus according to one embodiment of the present invention.

FIG. 1 is a block diagram illustrating the construction of a medical simulation apparatus according to one embodiment of the present invention. The medical simulation apparatus is adapted to perform a simulation with the use of a three-dimensional image, for example, for a surgical orthodontic operation in dental surgery or plastic surgery, and includes a unit body 1 incorporating a microprocessor and a hard disk therein.

The unit body 1 is connected to an input device 2 such as a keyboard and a mouse for inputting data and commands, a removable disk reader/writer 4 for writing and reading data with respect to a removable disk 3 such as a DVD (digital video disk), a display 5 for displaying a three-dimensional image, and a three-dimensional measuring instrument 7 for acquiring coordinates of a given point on a surface of an entity model 6 in a coordinate system defined by three predetermined points.

Figure 2:
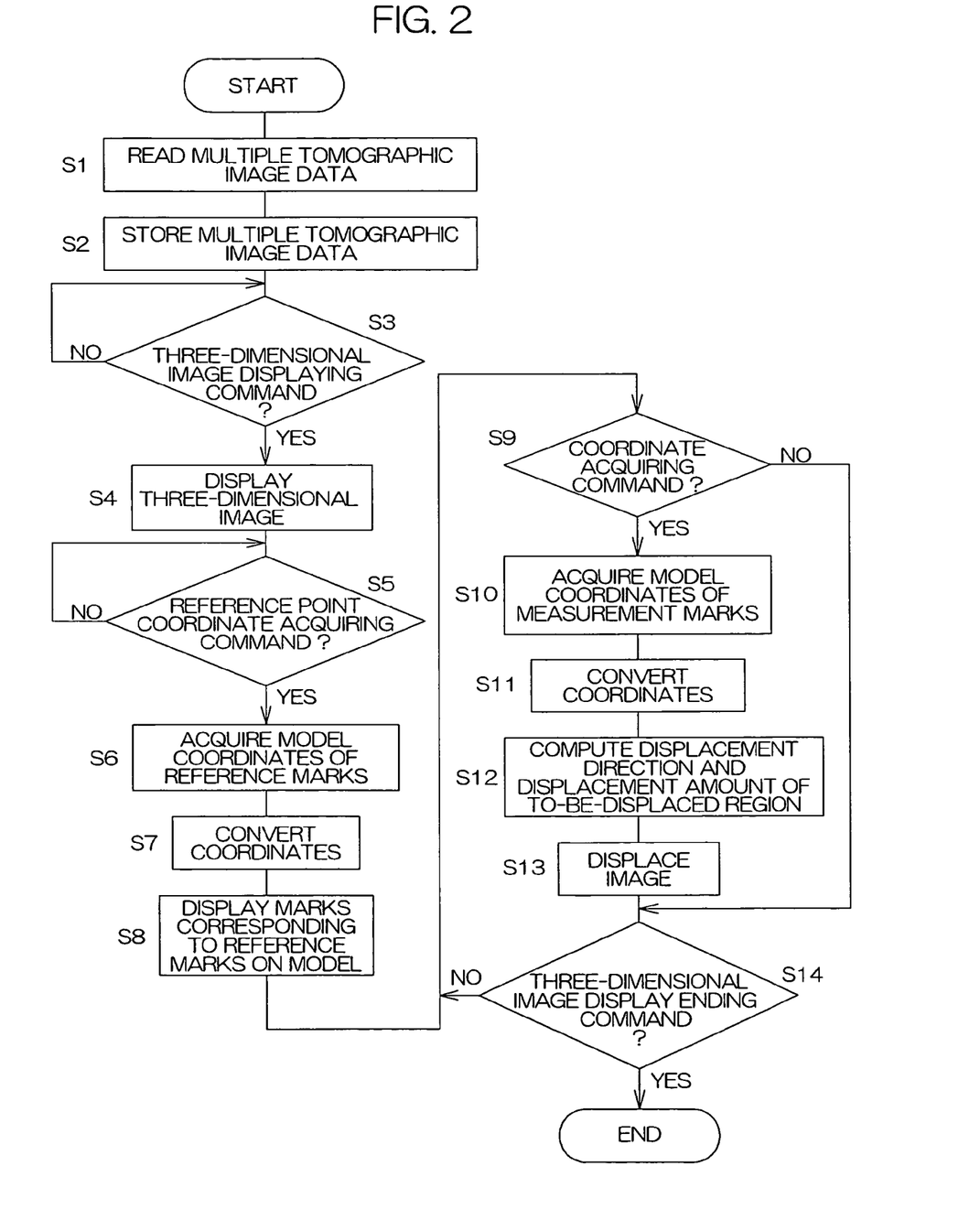
FIG. 2 is a flow chart illustrating the flow of a simulation process to be performed when a lower jawbone is to be displaced in a surgical orthodontic operation.

FIG. 2 is a flow chart illustrating the flow of a process for the simulation. Multiple tomographic image data of the head of a patient to be subjected to the surgical orthodontic operation is required for simulating the surgical orthodontic operation in the medical simulation apparatus.

The multiple tomographic image data is obtained, for example, by taking a multiplicity of tomograms by a tomographic apparatus such as a CT apparatus or an MRI apparatus, and inputted into the unit body 1 of the medical simulation apparatus via the removable disk 3. That is, the multiple tomographic image data obtained by the tomographic apparatus is written in the removable disk 3. The removable disk 3 containing the multiple tomographic image data written therein is set in the removable disk reader/writer 4. Upon input of a data reading command to the unit body 1 from the input device 2, the multiple tomographic image data is read out of the removable disk 3 by the removable disk reader/writer 4, and the multiple tomographic image data thus read out is applied to the unit body 1 (Step S1). Thus, the multiple tomographic image data read into the unit body 1 is stored in the hard disk incorporated in the unit body 1 (Step S2).

When a three-dimensional image displaying command is thereafter applied to the unit body 1 from the input device 2 (YES in Step S3), the multiple tomographic image data stored in the hard disk in the unit body 1 is stereographically reconstructed, and three-dimensional image data is generated. Then, a three-dimensional image of craniofacial bones of the patient's head is displayed on the display 5 on the basis of the three-dimensional image data (Step S4).

Figure 3:
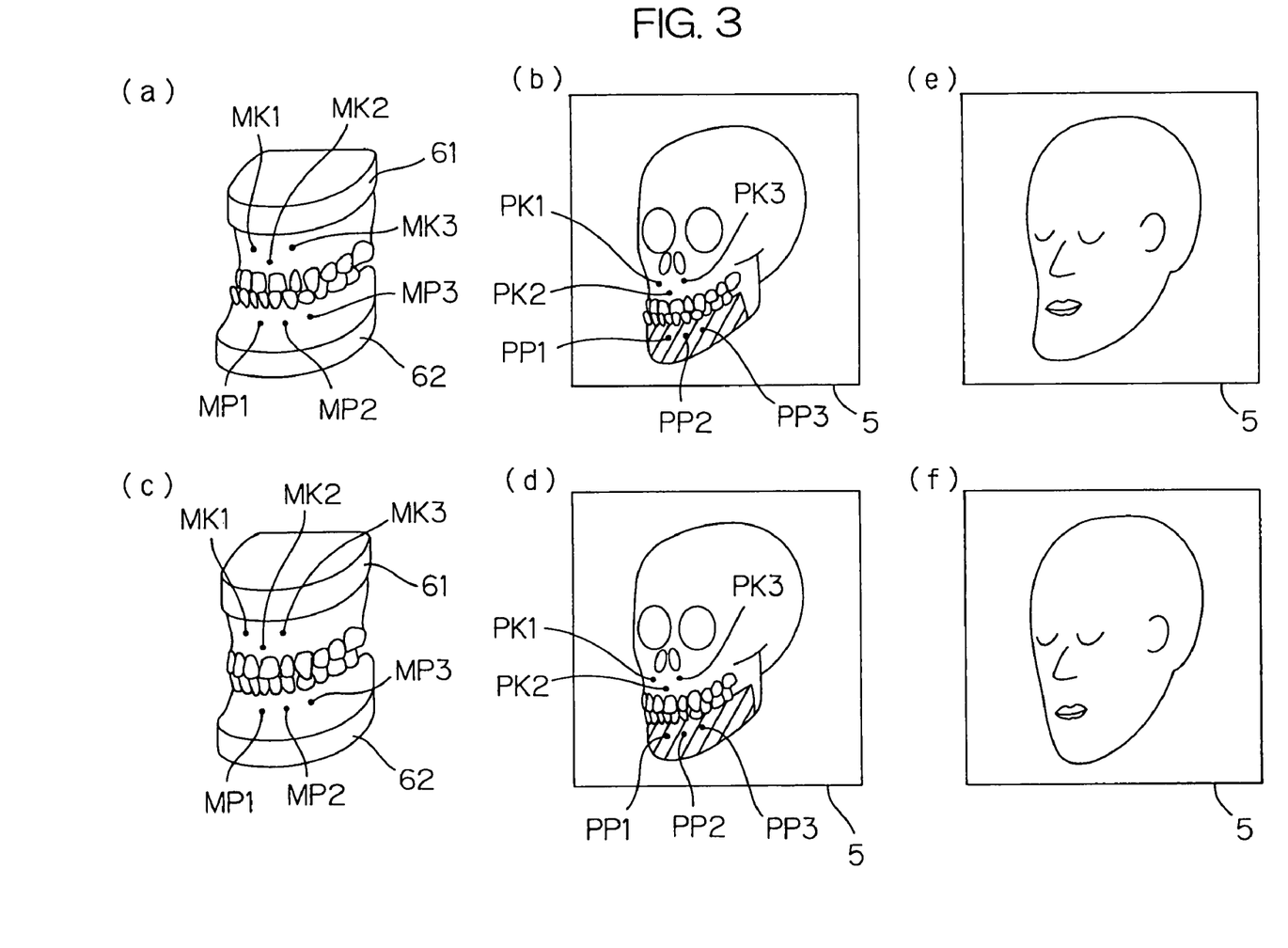
FIG. 3 are diagrams for explaining how to correlate an operation performed on an entity model with a three-dimensional image of a patient.

An upper dental arch model and a lower dental arch model (entity model) of the patient to be subjected to the surgical orthodontic operation are required for the simulation of the surgical orthodontic operation in the medical simulation apparatus. Therefore, an upper dental arch model 61 and a lower dental arch model 62 as shown in FIG. 3(*a*) are produced from gypsum plaster or a resin material on the basis of the entity of the patient before the start of the simulation. Three reference marks MK1, MK2, MK3 are provided on a surface of the upper dental arch model 61 as reference points for defining a coordinate system when acquiring coordinates by means of the three-dimensional measuring instrument 7. Further, three measurement marks MP1, MP2, MP3 are provided on a surface of the lower dental arch model 62.

A dentist or an operator fixes the upper dental arch model 61 at a predetermined position, and positions the lower dental arch model 62 with respect to the upper dental arch model 61 in the same occlusal relation as the current occlusal state of the patient. Thereafter, a reference point coordinate acquiring command is inputted into the unit body 1 by operating the input device 2. The dentist or the operator operates the input device 2 to put reference marks PK1, PK2, PK3 at positions corresponding to the reference marks MK1, MK2, MK3 provided on the upper dental arch model 61 in the three-dimensional image displayed on the display 5.

When the reference point coordinate acquiring command is inputted to the unit body 1 (YES in Step S5), the coordinates (hereinafter referred to as "model coordinates") of the measurement marks MP1, MP2, MP3 on the surface of the lower dental arch model 62 in the coordinate system defined by the three reference marks MK1, MK2, MK3 are acquired by the three-dimensional measuring instrument 7 (Step S6). The model coordinates of the measurement marks MP1, MP2, MP3 thus acquired are applied to the unit body 1, and converted into coordinates (hereinafter referred to as "image coordinates") in a coordinate system defined by the reference marks PK1, PK2, PK3 on the basis of a relationship between the reference marks MK1, MK2, MK3 and the reference marks PK1, PK2, PK3 (Step S7). Then, positions PP1, PP2, PP3 represented by the image coordinates obtained through the coordinate conversion are displayed on the three-dimensional image displayed on the display 5 as shown in FIG. 3(*b*) (Step S8).

Next, the dentist displaces the lower dental arch model 62 to a position at which protrusion of the upper jawbone or the lower jawbone or jaw deformity is corrected and the upper dental arch and the lower dental arch are kept in proper occlusal relation as shown in FIG. 3(*c*). Thereafter, the dentist or the operator operates the input device 2 to input a coordinate acquiring command to the unit body 1, and further operates the input device 2 to specify a region (hatched region) corresponding to the jawbone to be displaced by the surgical orthodontic operation on the three-dimensional image displayed on the display 5.

When the coordinate acquiring command is inputted to the unit body 1 after the displacement of the lower dental arch model 62 (YES in Step S9), the model coordinates of the measurement marks MP1, MP2, MP3 on the surface of the lower dental arch model 62 after the displacement are acquired by the three-dimensional measuring instrument 7 (Step S10). The model coordinates of the measurement marks MP1, MP2, MP3 thus acquired are applied to the unit body 1, and converted into image coordinates on the basis of the relationship between the reference marks MK1, MK2, MK3 and the reference marks PK1, PK2, PK3 (Step S11).

Thereafter, the displacement direction and displacement amount of the region (to-be-displaced region) of the three-dimensional image corresponding to the jawbone to be displaced by the surgical orthodontic operation are computed on the basis of changes in the image coordinates of the measurement marks MP1, MP2, MP3 after the displacement of the lower dental arch model 62 (Step S12). That is, the displacement directions and displacement amounts of all points within the to-be-displaced region of the three-dimensional image are computed according to the changes in the image coordinates of the measurement marks MP1, MP2, MP3. Then, the to-be-displaced region is displaced in the three-dimensional image as shown in FIG. 3(*d*) on the basis of the displacement directions and the displacement amounts thus computed (Step S13).

After the displacement of the region, it is judged whether or not a three-dimensional image display ending command is applied to the unit body 1 from the input device 2 (Step S14). If the three-dimensional image display ending command is not applied, the process returns to Step S9 to judge whether or not the coordinate acquiring command is applied to the unit body 1 from the input device 2. The judgment on the application of the coordinate acquiring command or the three-dimensional image display ending command is repeated until either the coordinate acquiring command or the three-dimensional image display ending command is applied. Then, if the coordinate acquiring command is applied in this period (YES in Step S9), the aforesaid process sequence from Step S10 to S13 is performed. If the three-dimensional image display ending command is applied (YES in Step S14), the simulation of the surgical orthodontic operation in the medical simulation apparatus is completed.

In the medical simulation apparatus, when the lower dental arch model 62 is displaced, the region preliminarily specified in the three-dimensional image of the patient displayed on the display 5 (the region corresponding to the jawbone to be displaced by the surgical orthodontic operation) is correspondingly displaced as described above. That is, in the medical simulation apparatus, functional information such as the contact state of the upper and lower dental arches can be reflected on the change in the three-dimensional image of the patient. Thus, the dentist can determine, on the basis of the display on the display 5, where the lower jawbone to be displaced by the surgical orthodontic operation is to be fixed, which tooth is to be displaced and how the tooth is to be displaced through postoperative orthodontics, in order to achieve an optimum occlusal state and an optimum morphological change of the entire head.

Further, the multiple tomographic image data of the patient's head includes image data of soft tissues such as skin and subcutaneous tissues, so that a three-dimensional image including an image of the soft tissues of the patient can be displayed on the display 5 as shown in FIG. 3(*e*) on the basis of the image data. Then, a region of the three-dimensional image corresponding to the jawbone to be displaced by the surgical orthodontic operation and the soft tissues associated with the jawbone is displaced in the three-dimensional image correspondingly to the displacement of the lower dental arch model 62, whereby the three-dimensional image including the image of the soft tissues of the patient after the operation is displayed on the display 5 as shown in FIG. 3(*f*). Thus, a change in the facial appearance of the patient attributable to the surgical orthodontic operation can easily be predicted and evaluated.

Figure 4:
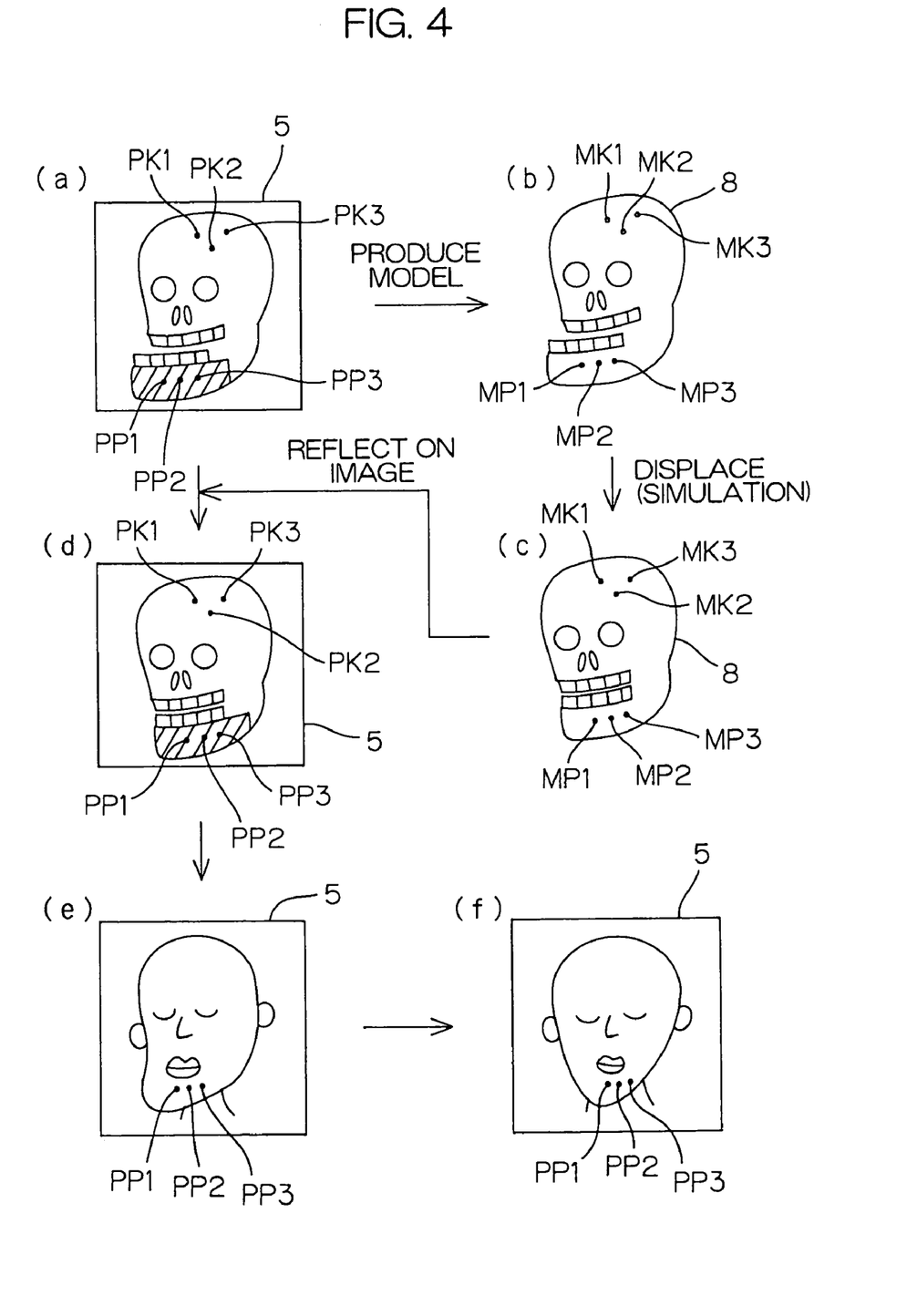
FIG. 4 are diagrams for explaining another embodiment of the present invention.

FIG. 4 are diagrams for explaining another embodiment of the present invention. In the aforesaid embodiment, the upper dental arch model 61 and the lower dental arch model 62 are produced as the entity model on the basis of the entity of the patient before the start of the simulation. In this embodiment, on the contrary, an entity model 8 of the craniofacial bones of the patient is produced on the basis of the three-dimensional image data generated by stereographic reconstruction of the multiple tomographic image data of the patient. Then, a simulation can be performed by correlating the entity model 8 with the three-dimensional image of the craniofacial bones.

That is, when the three-dimensional image displaying command is applied after the multiple tomographic image data is read into the unit body 1 (see FIG. 1), three-dimensional image data is generated on the basis of the multiple tomographic image data, and the resulting three-dimensional image of the craniofacial bones of the patient's head is displayed on the display 5 as shown in FIG. 4(*a*).

Thereafter, the dentist or the operator specifies a region (hatched region) corresponding to the jawbone to be displaced by the surgical orthodontic operation in the three-dimensional image displayed on the display 5. Then, three marks PP1, PP2, PP3 are inputted on the specified to-be-displaced region, and three reference marks PK1, PK2, PK3 are inputted in a region other than the specified to-be-displaced region for defining a coordinate system.

After the input of the marks PP1, PP2, PP3 and the reference marks PK1, PK2, PK3, three-dimensional image data including data of the marks PP1, PP2, PP3 and the reference marks PK1, PK2, PK3 is applied to a stereographic model producing apparatus (not shown). The stereographic model producing apparatus is adapted to produce a stereographic model, for example, by a photo-shaping method. Upon receiving the three-dimensional image data, the stereographic model producing apparatus produces the stereographic model (entity model) 8 of the craniofacial bones of the patient's head on the basis of the three-dimensional image data. Measurement marks MP1, MP2, MP3 and reference marks MK1, MK2, MK3 are respectively provided at positions corresponding to the marks PP1, PP2, PP3 and the reference marks PK1, PK2, PK3 on the produced entity model 8 as shown in FIG. 4(*b*)

Then, the dentist or the operator fixes, for example, a cranial portion of the entity model 8 at a predetermined position, and inputs the coordinate acquiring command to the unit body 1. Upon the input of the coordinate acquiring command to the unit body 1, the model coordinates of the measurement marks MP1, MP2, MP3 provided on the entity model 8 (in a coordinate system defined by the three reference marks MK1, MK2, MK3) are acquired by the three-dimensional measuring instrument 7 (see FIG. 1). The model coordinates of the measurement marks MP1, MP2, MP3 thus acquired are applied to the unit body 1, and converted into image coordinates (in a coordinate system defined by the reference marks PK1, PK2, PK3.) on the basis of a relationship between the reference marks MK1, MK2, MK3 and the reference marks PK1, PK2, PK3.

Thereafter, the dentist displaces a lower jawbone portion of the entity model 8 to a position at which protrusion of the upper jawbone or the lower jawbone or jaw deformity is corrected and the upper dental arch and the lower dental arch are kept in proper occlusal relation as shown in FIG. 4(*c*), and inputs the coordinate acquiring command to the unit body 1. Upon the input of the coordinate acquiring command to the unit body 1, the model coordinates of the measurement marks MP1, MP2, MP3 after the displacement are acquired by the three-dimensional measuring instrument 7. The model coordinates of the measurement marks MP1, MP2, MP3 thus acquired are applied to the unit body 1, and converted into image coordinates on the basis of the relationship between the reference marks MK1, MK2, MK3 and the reference marks PK1, PK2, PK3.

Then, the displacement direction and displacement amount of the to-be-displaced region previously specified in the three-dimensional image are computed on the basis of changes in the image coordinates of the measurement marks MP1, MP2, MP3 after the displacement of the lower jawbone portion of the entity model 8. That is, the displacement directions and displacement amounts of all points within the to-be-displaced region of the three-dimensional image are computed in accordance with the changes in the image coordinates of the measurement marks MP1, MP2, MP3. Then, the to-be-displaced region is displaced in the three-dimensional image as shown in FIG. 4(*d*) on the basis of the displacement directions and displacement amounts thus computed.

Therefore, the dentist can determine, on the basis of the change in the three-dimensional image after the displacement of the entity model 8, where the lower jawbone to be displaced by the surgical orthodontic operation is to be fixed, which tooth is to be displaced and how the tooth is to be displaced through postoperative orthodontics, in order to achieve an optimum occlusal state and an optimum morphological change of the entire head. Further, three-dimensional images each including an image of the soft tissues of the patient before and after the operation are displayed on the display 5 as shown in FIGS. 4(*e*) and 4(*f*) on the basis of image data of the soft tissues included in the multiple tomographic image data of the patient's head. Thus, a change in the facial appearance of the patient attributable to the surgical orthodontic operation can easily be predicted and evaluated.

Although the explanation has thus been given to the simulations to be performed when the lower jawbone is to be displaced by the surgical orthodontic operation in the two embodiments of the present invention, it is possible to perform any other simulations.

Figure 5:
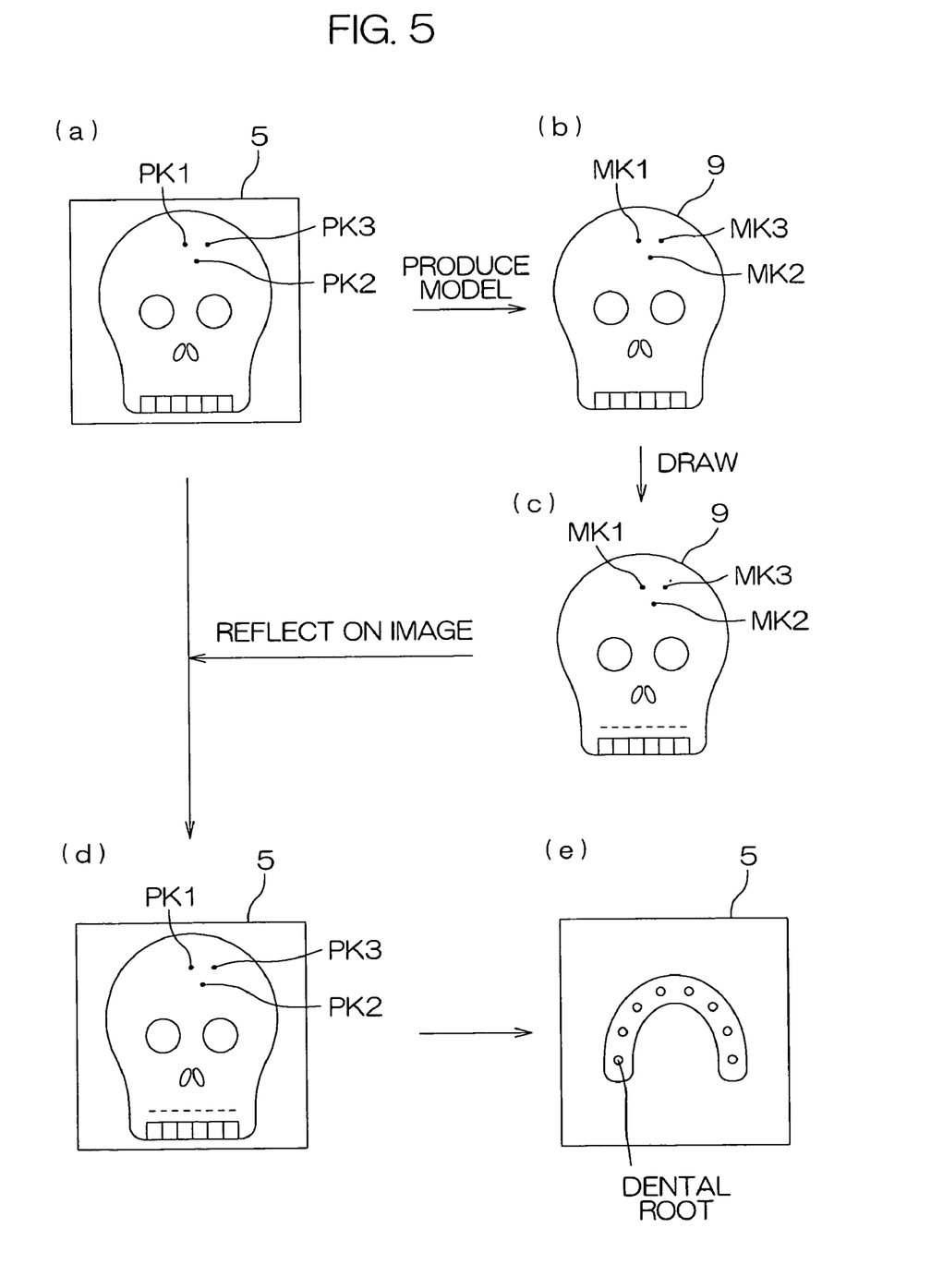
FIG. 5 are diagrams for explaining another simulation.

For example, after a three-dimensional image of the craniofacial bones is displayed on the display 5 as shown in FIG. 5(*a*), an entity model 9 according to the three-dimensional image as shown in FIG. 5(*b*) is produced by a photo-shaping method. Thereafter, an abscission line for the surgical operation is drawn on the entity model 9 as indicated by a broken line in FIG. 5(*c*). Then, the model coordinates of points on the abscission line thus drawn are acquired by the three-dimensional measuring instrument 7 (see FIG. 1), and the model coordinates thus acquired are applied to the unit body 1 (see FIG. 1), whereby a line corresponding to the abscission line drawn on the entity model 9 is displayed in the three-dimensional image as shown in FIG. 5(*d*). Thus, the abscission line can be displayed at a more accurate position in the three-dimensional image than in the case where the dentist or the operator manually draws an abscission line in the three-dimensional image (e.g., by operating the mouse) while viewing the abscission line drawn on the entity model 9. Further, a sectional image taken along the abscission line displayed in the three-dimensional image can be displayed on the display 5 as shown in FIG. 5(*e*) on the basis of the multiple tomographic image data taken into the unit body 1 for displaying the three-dimensional image. This makes it possible to predict an influence of the abscission and the like and determine an optimum abscission position.

Figure 6:
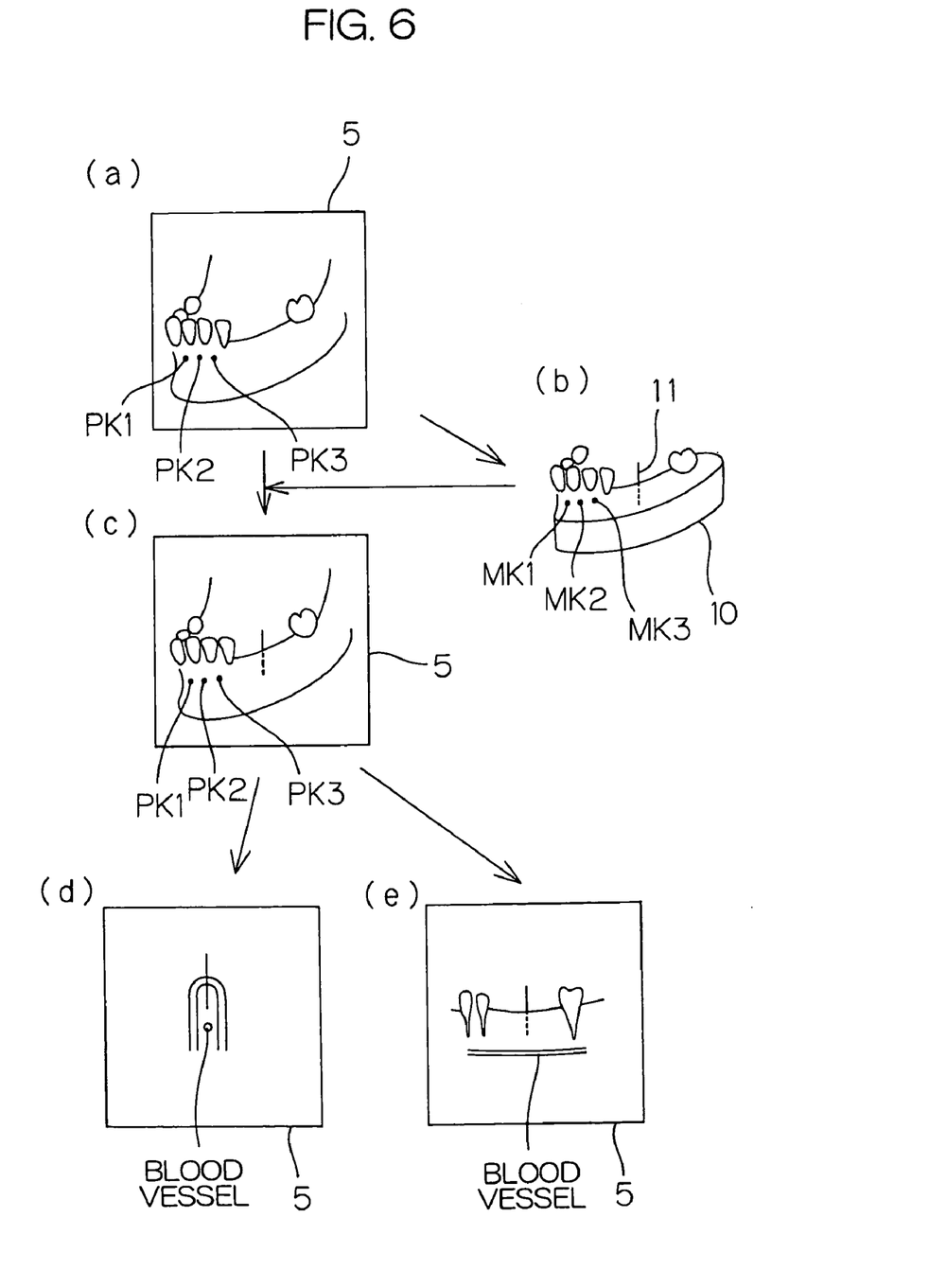
FIG. 6 are diagrams for explaining further another simulation.

It is also possible to perform a simulation of implantation of a dental implant. Where the dental implant is to be implanted in the lower jawbone, for example, a three-dimensional image of the lower jawbone is displayed on the display 5 as shown in FIG. 6(*a*) on the basis of the multiple tomographic image data, and then an entity model 10 according to the three-dimensional image is produced by a photo-shaping method. In turn, a dental implant 11 having a predetermined length is implanted in the entity model 10 as shown in FIG. 6(*b*). Thereafter, the model coordinates of an upper end point of the dental implant 11 and the model coordinates of an implantation point (insertion point) are acquired by the three-dimensional measuring instrument 7 (see FIG. 1), and the model coordinates thus acquired are applied to the unit body 1 (see FIG. 1). Then, the model coordinates of the upper end point of the dental implant 11 and the implantation point are converted into image coordinates in the unit body 1, and an image of the dental implant 11 is displayed together with the three-dimensional image as shown in FIG. 6(*c*) on the basis of the image coordinates of the upper end point of the dental implant 11 and the implantation point obtained by the coordinate conversion and data of the length of the dental implant 11 preliminarily inputted. This makes it possible to check if the implantation direction and depth of the dental implant 11 is appropriate, while viewing the display 5, and to properly determine the implantation direction and depth of the dental implant 11. It is also possible to confirm a positional relationship between the dental implant and tissues (a blood vessel and the like) which should not be damaged, while displaying a sectional image of the lower jawbone on the display 5 as shown in FIGS. 6(*d*) and 6(*e*) on the basis of the multiple tomographic image data taken into the unit body 1 for displaying the three-dimensional image.

Other various modifications may be made within the scope of the present invention defined by the claims.

What is claimed is:

1. A medical simulation apparatus, comprising:

an image display means that displays a three-dimensional image of a patient; and a display controlling means that correlates an entity model of the patient with the three-dimensional image by utilizing at least three reference points on the entity model and at least three reference points on the three-dimensional image, and changes the three-dimensional image according to a change in the entity model;

wherein the change in the entity model includes displacing a predetermined portion of the entity model, wherein the display controlling means determines changes in coordinates of points on the three-dimensional image corresponding to at least three points on the predetermined portion after the displacement of the predetermined portion on the basis of a relationship between the reference points on the entity model and the reference points on the three-dimensional image, and displaces a region of the three-dimensional image corresponding to the predetermined portion on the basis of the determined coordinate changes, wherein the entity model is a model formed of gypsum plaster or a resin material on the basis of the entity of the patient, and wherein the predetermined portion corresponds to a portion of the entity of the patient to be displaced by a surgical operation.

2. A medical simulation apparatus as set forth in claim 1, wherein the change in the entity model includes providing a dot or a line on the entity model, wherein the display controlling means determines coordinates of a point or points on the three-dimensional image corresponding to the dot or points on the line provided on the entity model on the basis of the relationship between the reference points on the entity model and the reference points on the three-dimensional image, and displays an image of the dot or the line provided on the entity model in the three-dimensional image on the basis of the determined point coordinates.

3. A medical simulation apparatus, comprising:

an image display means that displays a three-dimensional image of a patient; and a display controlling means that correlates an entity model of the patient with the three-dimensional image by utilizing at least three reference points on the entity model and at least three reference points on the three-dimensional image, and changes the three-dimensional image according to a chance in the entity model;

wherein the change in the entity model includes displacing a predetermined portion of the entity model, wherein the display controlling means determines changes in coordinates of points on the three-dimensional image corresponding to at least three points on the predetermined portion after the displacement of the predetermined portion on the basis of a relationship between the reference points on the entity model and the reference points on the three-dimensional image, and displaces a region of the three-dimensional image corresponding to the predetermined portion on the basis of the determined coordinate changes, wherein the entity model comprises upper and lower dental arch models, wherein the predetermined portion is the upper dental arch model or the lower dental arch model, wherein the entity model is a model formed of gypsum plaster or a resin material on the basis of the entity of the patient, and wherein the predetermined portion corresponds to a portion of the entity of the patient to be displaced by a surgical operation.

4. A medical simulation apparatus, as set forth in claim 3, wherein the change in the entity model includes providing a dot or a line on the entity model, wherein the display controlling means determines coordinates of a point or points on the three-dimensional image corresponding to the dot or points on the line provided on the entity model on the basis of the relationship between the reference points on the entity model and the reference points on the three-dimensional image, and displays an image of the dot or the line provided on the entity model in the three-dimensional image on the basis of the determined point coordinates.

\* \* \* \* \*